US008825142B2

(12) United States Patent
Suehara

(10) Patent No.: US 8,825,142 B2
(45) Date of Patent: Sep. 2, 2014

(54) IMAGING APPARATUS FOR DIAGNOSIS AND CONTROL METHOD THEREOF

(75) Inventor: Satoru Suehara, Matsuda-machi (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 151 days.

(21) Appl. No.: 13/499,075

(22) PCT Filed: Sep. 14, 2010

(86) PCT No.: PCT/JP2010/005605
§ 371 (c)(1),
(2), (4) Date: Apr. 11, 2012

(87) PCT Pub. No.: WO2011/039956
PCT Pub. Date: Apr. 7, 2011

(65) Prior Publication Data
US 2012/0190974 A1 Jul. 26, 2012

(30) Foreign Application Priority Data

Sep. 30, 2009 (JP) ................................ 2009-227840

(51) Int. Cl.
A61B 6/00 (2006.01)
A61B 5/00 (2006.01)
G02B 6/42 (2006.01)
G01B 9/02 (2006.01)
G02B 6/32 (2006.01)
G02B 6/26 (2006.01)
A61B 1/00 (2006.01)
G01N 21/17 (2006.01)
G01J 3/453 (2006.01)
G02B 6/36 (2006.01)

(52) U.S. Cl.
CPC ............. A61B 5/0066 (2013.01); A61B 5/0073 (2013.01); A61B 5/6852 (2013.01); A61B 1/00112 (2013.01); G01N 21/17 (2013.01); G01J 3/453 (2013.01); G02B 6/3604 (2013.01); G02B 6/4219 (2013.01)
USPC ......... 600/476; 356/455; 385/33; 250/227.24

(58) Field of Classification Search
USPC ......... 356/455; 600/476; 385/33; 250/227.24
See application file for complete search history.

(56) References Cited

U.S. PATENT DOCUMENTS 5,588,077 A * 12/1996 Woodside ........................ 385/26
5,872,879 A * 2/1999 Hamm ............................ 385/25
(Continued)

FOREIGN PATENT DOCUMENTS

EP 2062526 A1 5/2009
JP 2000-97845 A 4/2000
(Continued)

OTHER PUBLICATIONS

International Search Report (PCT/ISA/210) issued on Nov. 2, 2010, by Japanese Patent Office as the International Searching Authority for International Application No. PCT/JP2010/005605.
(Continued)

Primary Examiner — Long V. Le
Assistant Examiner — Angela M Hoffa
(74) Attorney, Agent, or Firm — Buchanan Ingersoll & Rooney

(57) ABSTRACT

An imaging apparatus for diagnosis is connected with a probe including a transmitting and receiving unit transmitting a light transmitted from a light source continuously to the inside of a body cavity and concurrently, receiving a reflected light continuously from the inside of the body cavity, and generates a tomographic image inside the body cavity based on the obtained reflected light by obtaining the reflected light from the transmitting and receiving unit while rotating the transmitting and receiving unit. The apparatus includes a mechanism for extracting intensity of the reflected light obtained by a phenomenon that the light transmitted to the transmitting and receiving unit is reflected at the transmitting and receiving unit; and a mechanism for judging whether or not the extracted intensity of each reflected light at each rotary angle of the transmitting and receiving unit lies in a range of a predetermined variation width.

10 Claims, 13 Drawing Sheets

(56) References Cited

U.S. PATENT DOCUMENTS

| | | | |
|---|---|---|---|
| 7,180,600 B2* | 2/2007 | Horii et al. | 356/479 |
| 7,325,977 B2* | 2/2008 | Stevens | 385/60 |
| 8,040,524 B2* | 10/2011 | Ozawa | 356/479 |
| 8,055,107 B2* | 11/2011 | Masuda | 385/26 |
| 8,265,434 B2* | 9/2012 | Popp et al. | 385/26 |
| 8,622,893 B2* | 1/2014 | Mathieu | 600/132 |
| 2003/0004412 A1 | 1/2003 | Izatt et al. | |
| 2006/0058592 A1 | 3/2006 | Bouma et al. | |
| 2007/0024839 A1 | 2/2007 | Kawakami et al. | |
| 2007/0244391 A1 | 10/2007 | Hirota | |

FOREIGN PATENT DOCUMENTS

| | | |
|---|---|---|
| JP | 2004-205774 A | 7/2004 |
| JP | 2007-36016 A | 2/2007 |
| JP | 2007-268132 A | 10/2007 |
| JP | 2008-14914 A | 1/2008 |
| JP | 2008-253492 A | 10/2008 |
| JP | 2009-25640 A | 2/2009 |
| JP | 2009-60460 A | 3/2009 |
| JP | 2009-178200 A | 8/2009 |
| JP | 2009-183416 A | 8/2009 |

OTHER PUBLICATIONS

Extended European Search Report dated Mar. 17, 2014, issued by the European Patent Office in corresponding European Patent Application No. 10820082.5. (6 pages).

* cited by examiner

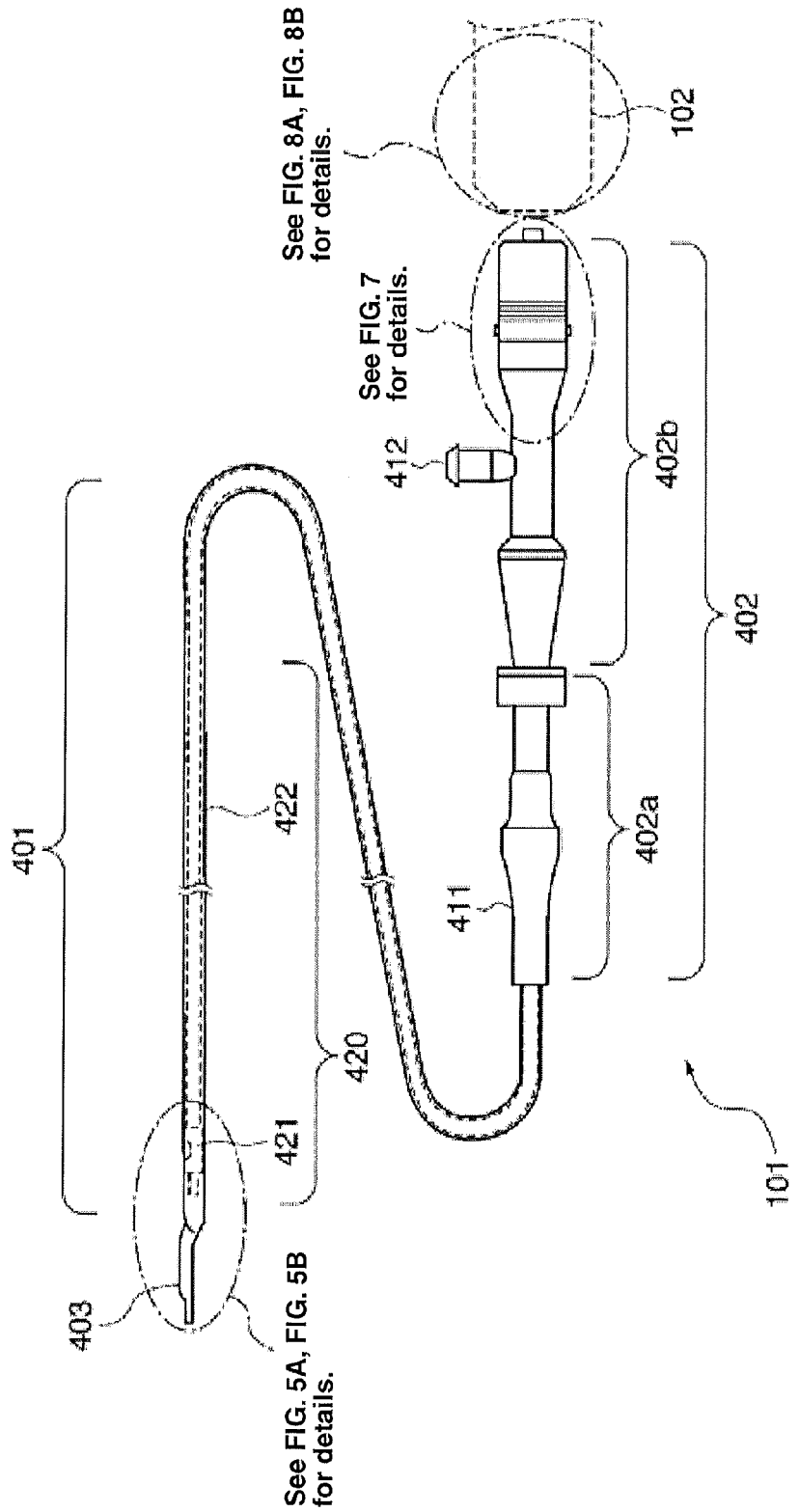

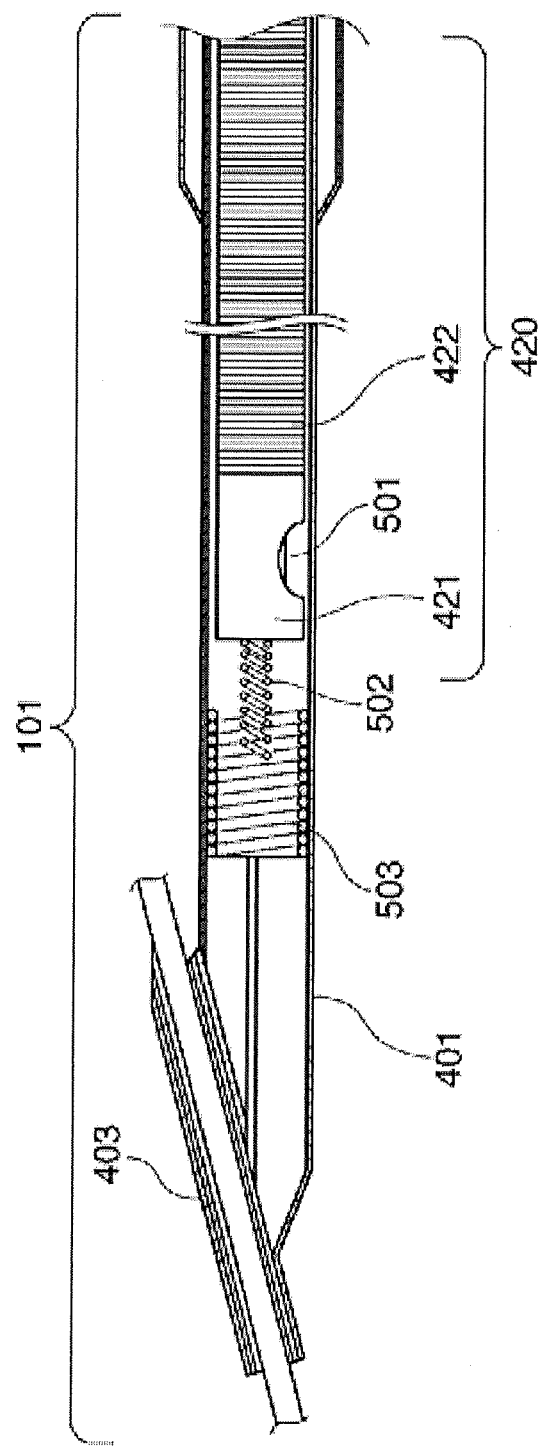

IMAGING APPARATUS FOR DIAGNOSIS AND CONTROL METHOD THEREOF

TECHNICAL FIELD

The present invention relates to an imaging apparatus for diagnosis and a control method thereof.

BACKGROUND ART

From the past, in an imaging apparatus for diagnosis such as an optical coherent tomography (OCT) apparatus for diagnosis, an optical frequency domain imaging (OFDI) apparatus for diagnosis utilizing wavelength sweep and the like, there has been used, as a probe inserted inside a body cavity such as a blood vessel, an optical probe unit which is installed with a transmitting and receiving unit carrying out optical transmission and reception and an optical fiber (for example, see Japanese unexamined patent publication No. 2000-097845).

In the imaging apparatus for diagnosis, in order to achieve a radial scan inside a body cavity by the transmitting and receiving unit, there is carried out an operation in which while rotating the transmitting and receiving unit in a state of inserting the optical probe unit inside the body cavity, the unit is moved in an distal direction and in an opposite direction thereof (axial direction) inside the body cavity.

In order to realize a radial operation of such a transmitting and receiving unit, a scanner & pull-back unit is usually provided in the imaging apparatus for diagnosis. Then, there are provided, in the scanner & pull-back unit, with a rotational drive unit for rotating the transmitting and receiving unit and the optical fiber installed in the optical probe unit while moving them in the axial direction and with a fixed unit connected optically to a main body control unit of the imaging apparatus for diagnosis, and an optical transmission by a photo coupling unit is carried out between the rotational drive unit and the fixed unit.

DISCLOSURE OF THE INVENTION

Problem to be Solved by the Invention

When the optical axis on the rotational drive unit side and the optical axis of the fixed unit side deviate in the scanner & pull-back unit including such a photo coupling unit, it becomes impossible, in the radial scan, to transmit the measurement light from the main body control unit accurately with respect to the transmitting and receiving unit and also, it becomes impossible to transmit the reflected light from the transmitting and receiving unit accurately with respect to the main body control unit and therefore, it becomes a situation in which there occurs such a problem that the picture quality of the generated tomographic image deteriorates.

Consequently, on an occasion when carrying out the radial scan, it is desirable to able to confirm beforehand a fact that the optical axis on the rotational drive unit side in the photo coupling unit coincides with the optical axis on the fixed unit side therein.

However, in a conventional imaging apparatus for diagnosis, there was not employed a constitution in which it is possible to confirm the deviation between the optical axis on the rotational drive unit side in the photo coupling unit and the optical axis on the fixed unit side therein, and there was a possibility that deterioration in the picture quality of the tomographic image, which is caused by the deviation of the optical axis, may be incurred.

The present invention was invented in view of the problem mentioned above and has an object to make it possible to confirm the deviation of the optical axis of the photo coupling unit in the scanner & pull-back unit in the imaging apparatus for diagnosis.

Means for Solving the Problem

In order to achieve the object mentioned above, an imaging apparatus for diagnosis relating to the present invention is provided with such a constitution as follows. More specifically, there is disclosed an imaging apparatus for diagnosis which is connected with a probe including a transmitting and receiving unit transmitting a light transmitted from a light source continuously to the inside of a body cavity and concurrently, receiving a reflected light continuously from the inside of the body cavity, and which generates a tomographic image inside the body cavity based on the obtained reflected light by obtaining the reflected light from the transmitting and receiving unit while rotating the transmitting and receiving unit and moving it toward the axial direction inside a body cavity, characterized by including:

extraction means extracting intensity of the reflected light, within the reflected lights obtained from the transmitting and receiving unit at respective rotary angles of the transmitting and receiving unit during rotation, obtained by a phenomenon that the light transmitted to the transmitting and receiving unit is reflected at the transmitting and receiving unit; and judgment means judging whether or not the intensity of each reflected light extracted by the extraction means at each rotary angle of the transmitting and receiving unit lies in a range of a predetermined variation width.

Effect of the Invention

According to the present invention, it becomes possible to confirm the deviation of the optical axis of the photo coupling unit in the scanner & pull-back unit in the imaging apparatus for diagnosis.

Other features and advantages of the present invention will become clear according to the following explanations with reference to the attached drawings. Note that, in the attached drawings, identical reference numbers are to be attached for the identical or similar constitutions.

BRIEF DESCRIPTION OF DRAWINGS

The attached drawings are included in the specification, constitute a portion thereof, show exemplified embodiments of the present invention, and are used together with the description thereof for explaining principles of the present invention.

FIG. 4 is a diagram showing a whole constitution of an optical probe unit;

FIG. 5A is a diagram showing a constitution of a distal end portion of an optical probe unit;

MODE FOR CARRYING OUT THE INVENTION

Hereinafter, exemplified embodiments of the present invention will be explained in detail with reference to the attached drawings if necessary.

First Exemplified Embodiment

<1. Outward-Appearance Constitution of Imaging Apparatus for Diagnosis>

Figure 1:
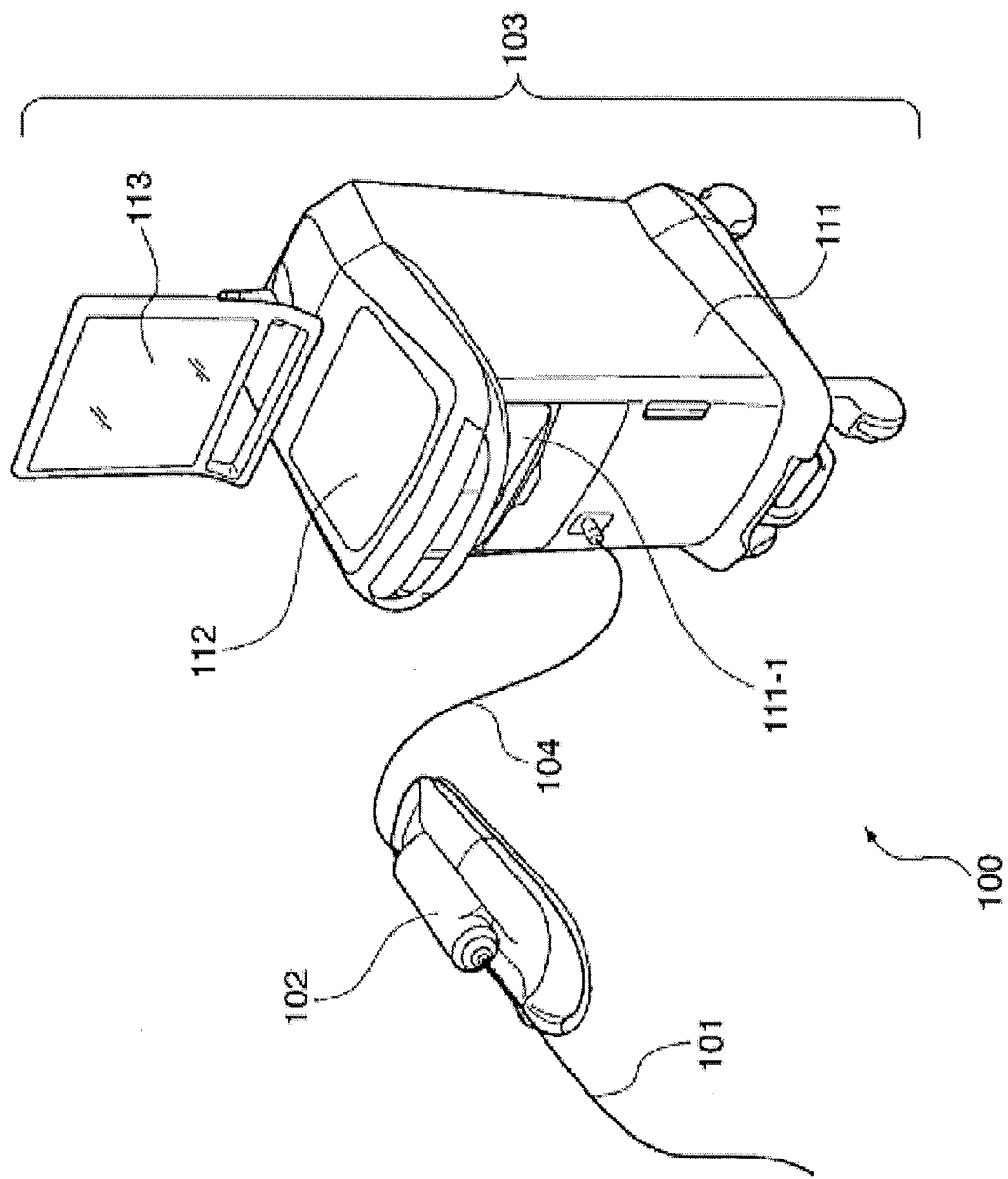
FIG. 1 is a diagram showing an outward-appearance constitution of an imaging apparatus for diagnosis relating to a first exemplified embodiment of the present invention.

FIG. 1 is a diagram showing an outward-appearance constitution of an optical imaging apparatus for diagnosis (optical coherent tomography apparatus or optical frequency domain imaging apparatus utilizing wavelength sweep) 100 relating to a first exemplified embodiment of the present invention.

As shown in FIG. 1, the imaging apparatus for diagnosis 100 is provided with an optical probe unit 101, a scanner & pull-back unit 102 and an operation control apparatus 103, and the scanner & pull-back unit 102 and the operation control apparatus 103 are connected by means of a signal line 104.

The optical probe unit 101 is inserted directly into a body cavity such as a blood vessel or the like and a state inside the body cavity is measured by using an imaging core which will be described later. The scanner & pull-back unit 102 is constituted detachably with respect to the optical probe unit 101 and defines the radial operation of the imaging core inside the optical probe unit 101 by a mechanism in which a built-in motor is driven.

The operation control apparatus 103 is provided with a function for inputting various kinds of set values on an occasion when carrying out the optical coherent tomographic diagnosis inside the body cavity, and a function for processing data obtained by the measurement and for displaying them as tomographic images.

In the operation control apparatus 103, a reference numeral 111 indicates a main body control unit, and data obtained by the measurement are processed, the processed result is outputted therein and so on. A reference numeral 111-1 indicates a printer & DVD recorder and the processed result in the main body control unit 111 is printed, is stored as data signals and so on.

A reference numeral 112 indicates an operation panel and a user carries out input of various kinds of set values and instruction through the operation panel 112. A reference numeral 113 indicates an LCD monitor as a display apparatus and it displays the processed result in the main body control unit 111.

<2. Functional Constitution of Optical Coherent Tomography Apparatus for Diagnosis>

Figure 2:
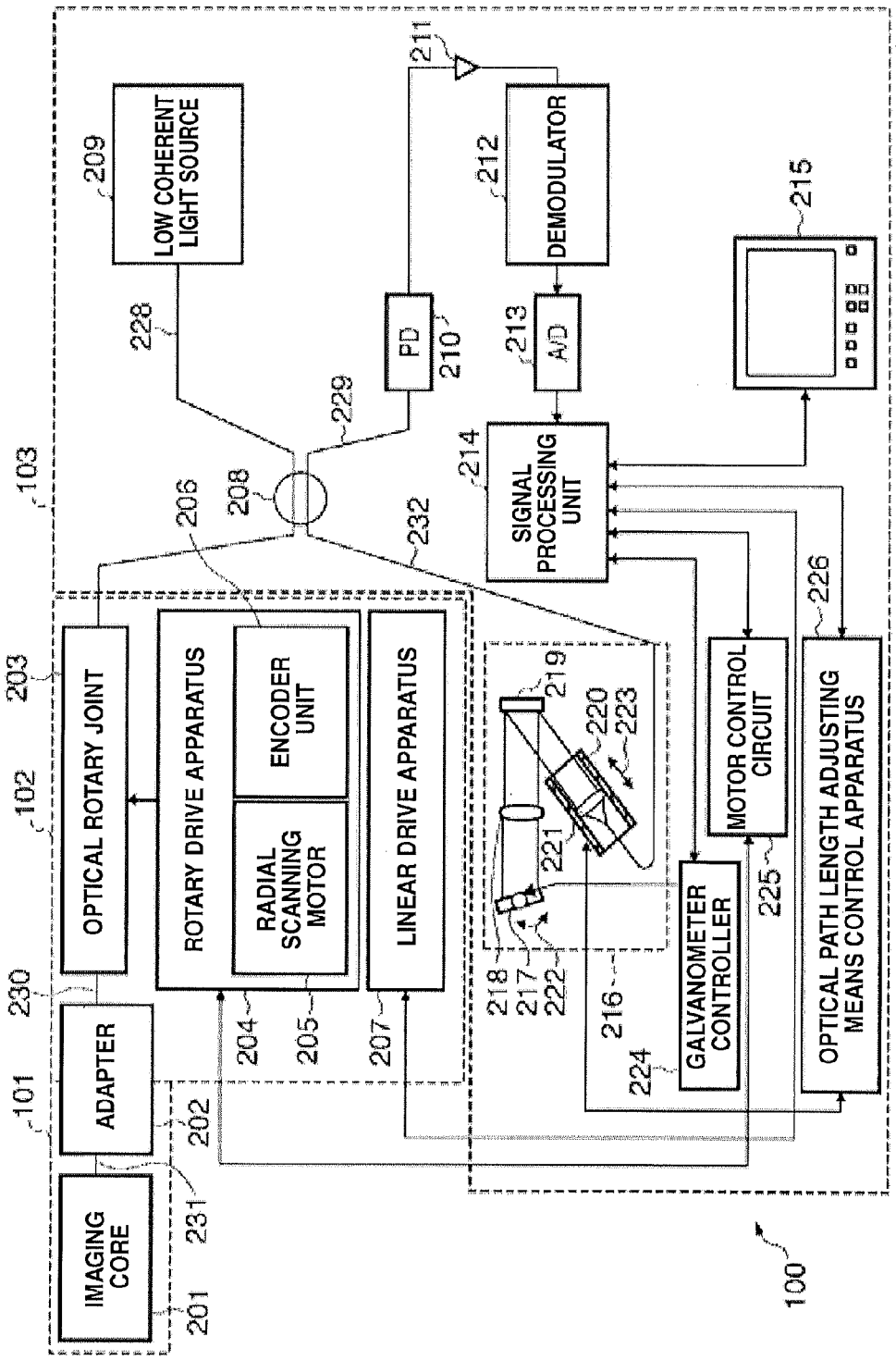
FIG. 2 is a diagram showing a functional constitution of an optical coherent tomography imaging apparatus for diagnosis 100.

Next, within the imaging apparatus for diagnosis 100 relating to this exemplified embodiment, it will be explained, by using FIG. 2, with respect to a main functional constitution of the optical coherent tomography apparatus.

A reference numeral 209 indicates a low coherent light source of a super high luminance light-emitting diode or the like. The low coherent light source 209 outputs a low coherent light which presents coherence only in such a short distance range that the wavelength thereof is around 1310 nm and the coherent-able distance (coherent length) thereof is around several μm to ten and several μm.

Consequently, in a case in which this light is split into two lights and thereafter, again mixing them, it happens that it is detected as interference light in a case in which difference of the two optical path lengths from the split point to the mixed point is within a short distance range of around several tun to ten and several μm, and in a case in which the difference of the optical path lengths is larger than that, it is never detected as interference light.

The light of the low coherent light source 209 is entered to one end of a first single mode fiber 228 and is transmitted to the distal end surface side. The first single mode fiber 228 is coupled with second single mode fiber 229 and third single mode fiber 232 optically by a photo coupler unit 208 on the way.

The photo coupler unit means an optical component which can split one optical signal into two or more outputs, which can couple two or more inputted optical signals into one output and the like, and it is possible for the light of the low coherent light source 209 to be transmitted by being split into maximum three optical paths depending on aforesaid photo coupler unit 208.

There is provided, on the distal end side from the photo coupler unit 208 of the first single mode fiber 228, the scanner & pull-back unit 102. There is provided, in the inside of the rotary drive apparatus 204 of the scanner & pull-back unit 102, with an optical rotary joint (photo coupling unit) 203 which couples between a non-rotation unit (fixed unit) and a rotation unit (rotational drive unit) and which transmits light.

Further, the distal end side of a fourth single mode fiber 230 inside the optical rotary joint 203 is connected freely detachably with a fifth single mode fiber 231 of the optical probe unit 101 through an adaptor 202. Thus, the light from the low coherent light source 209 is transmitted to the fifth single mode fiber 231 which is inserted into the inside of the imaging core 201 repeating transmission and reception of the light and which is drivable rotationally.

The light transmitted to the fifth single mode fiber 231 is illuminated with respect to the biological tissue inside the blood vessel from the distal end side of the imaging core 201 while being operated radially. Then, a portion of the reflected light scattered at the surface or in the inside of the biological tissue is taken-in by the imaging core 201 and returns to the first single mode fiber 228 side by way of the opposite optical path, and a portion thereof is moved to the second single mode fiber 229 side by the photo coupler unit 208. Then, it is emanated from one end of the second single mode fiber 229 and it is light-received by a photo detector (for example, photodiode 210).

Note that the rotational drive unit side of the optical rotary joint 203 is driven rotationally by a radial scanning motor 205 of a rotary drive apparatus 204. Also, the rotary angle of the radial scanning motor 205 is detected by an encoder unit 206. Further, the scanner & pull-back unit 102 is provided with a linear drive apparatus 207 and defines movement (axial direction motion) of the axial direction (distal direction inside the body cavity and opposite direction thereof) of the imaging core 201 based on an instruction from a signal processing unit 214. The axial direction motion is realized by a fact that the linear drive apparatus 207 moves a scanner including an optical rotary joint 203 based on a control signal from the signal processing unit 214.

At that time, the axial-direction movement is carried by without injuring a blood vessel wall depending on the fact that only the imaging core 201 inserted into a catheter sheath moves axially while the catheter sheath of the optical probe unit 101 is maintained to be fixed in the blood vessel.

On the other hand, there is provided, on the distal end side (reference light path) from the photo coupler unit 208 of the second single mode fiber 229, with a variable mechanism of optical path length 216 for changing the optical path length of the reference light.

This variable mechanism of optical path length 216 is provided with a first optical path length changing means for high-speedily changing the optical path length corresponding to an inspection range in the depth direction (emission direction of measurement light) of the biological tissue, and a second optical path length changing means for changing the optical path length corresponding to fluctuation of the length thereof so as to be able to absorb fluctuation of the length of individual optical probe unit 101 in case of using an optical probe unit 101 by being exchanged.

There is arranged a mirror 219 which is facing to the distal end of the third single mode fiber 232 and which is mounted on an one-axis stage 220 together with this distal end, through a collimating lens 221 freely movable in the direction shown by an arrow 223. Also, there is mounted a minute angle rotatable galvanometer 217 as a first optical path length changing means through this mirror 219 (diffraction grating) and a corresponding lens 218. This galvanometer 217 is rotated high-speedily in an arrow 222 direction depending on a galvanometer controller 224.

The galvanometer 217 is a device which reflects light by a mirror of the galvanometer and it is constituted such that the mirror mounted on a movable portion thereof is to be rotated speedily by applying an AC drive signal to the galvanometer which functions as a reference mirror.

More specifically, a drive signal is applied with respect to the galvanometer 217 from the galvanometer controller 224 and by rotating high-speedily in the arrow 222 direction caused by the drive signal, it happens that the optical path length of the reference light changes high-speedily as much as the optical path length corresponding to an inspection range in the depth direction of the biological tissue. One cycle of this change of the optical path difference becomes a period for obtaining the interference light for one line.

On the other hand, the one-axis stage 220 functions as the second optical path length changing means having such an amount of variable range of optical path length, which can absorb the fluctuation of the optical path length of the optical probe unit 101 in case of exchanging the optical probe unit 101. Further, the one-axis stage 220 is also provided with a function as an adjusting means for adjusting an offset. For example, even in a case in which the distal end of the optical probe unit 101 is not closely-attached to the surface of the biological tissue, it is possible, by changing the optical path length by the one-axis stage 220, to set it in a state of interfering with the reflected light from the surface position of the biological tissue.

The light whose optical path length is changed by the variable mechanism 216 of the optical path length is mixed with the light obtained from the first single mode fiber 228 side by the photo coupler unit 208 which is provided on the way of the third single mode fiber 232 and is light-received as interference light by the photo diode 210.

In this manner, the interference light received by the photodiode 210 is photoelectrically converted and amplified by the amplifier 211.

Thereafter, it is inputted to the demodulator 212 and in the demodulator 212, a demodulation process for extracting only the optical signal component of the interfering light is carried out, and the output thereof is inputted to the A/D converter 213.

In the A/D converter 213, the interference light signal is subjected to sampling, for example, by 200 points and digital data of one line ("interference light data") are generated. In this case, the sampling frequency becomes a value dividing one scan time period of the optical path length by 200.

The interference light data of one line unit which are generated in the A/D converter 213 are inputted to a signal processing unit 214. In the signal processing unit 214, tomographic images at respective positions inside the blood vessel are generated by converting the interference light data in the depth direction of the biological tissue to video signals and they are outputted to an LCD monitor 215 (corresponding to reference numeral 113 in FIG. 1) by a predetermined frame rate.

The signal processing unit 214 is further connected with an optical path length adjusting means control apparatus 226. The signal processing unit 214 carries out position control of the one-axis stage 220 through the optical path length adjusting means control apparatus 226. Also, the signal processing unit 214 is connected with a motor control circuit 225 and controls the rotary drive of the radial scanning motor 405.

Also, the signal processing unit 214 is connected with a galvanometer controller 224 for controlling scan of the optical path length of the reference mirror (galvanometer mirror) and the galvanometer controller 224 outputs a drive signal to the signal processing unit 214. In the motor control circuit 225, synchronization is taken with the galvanometer controller 224 by using this drive signal.

<3. Functional Constitution of Optical Frequency Domain Imaging Apparatus Utilizing Wavelength Sweep>

Next, within the imaging apparatus for diagnosis 100 relating to this exemplified embodiment, it will be explained with respect to a main functional constitution of the optical frequency domain imaging apparatus utilizing wavelength sweep by using FIG. 3.

Figure 3:
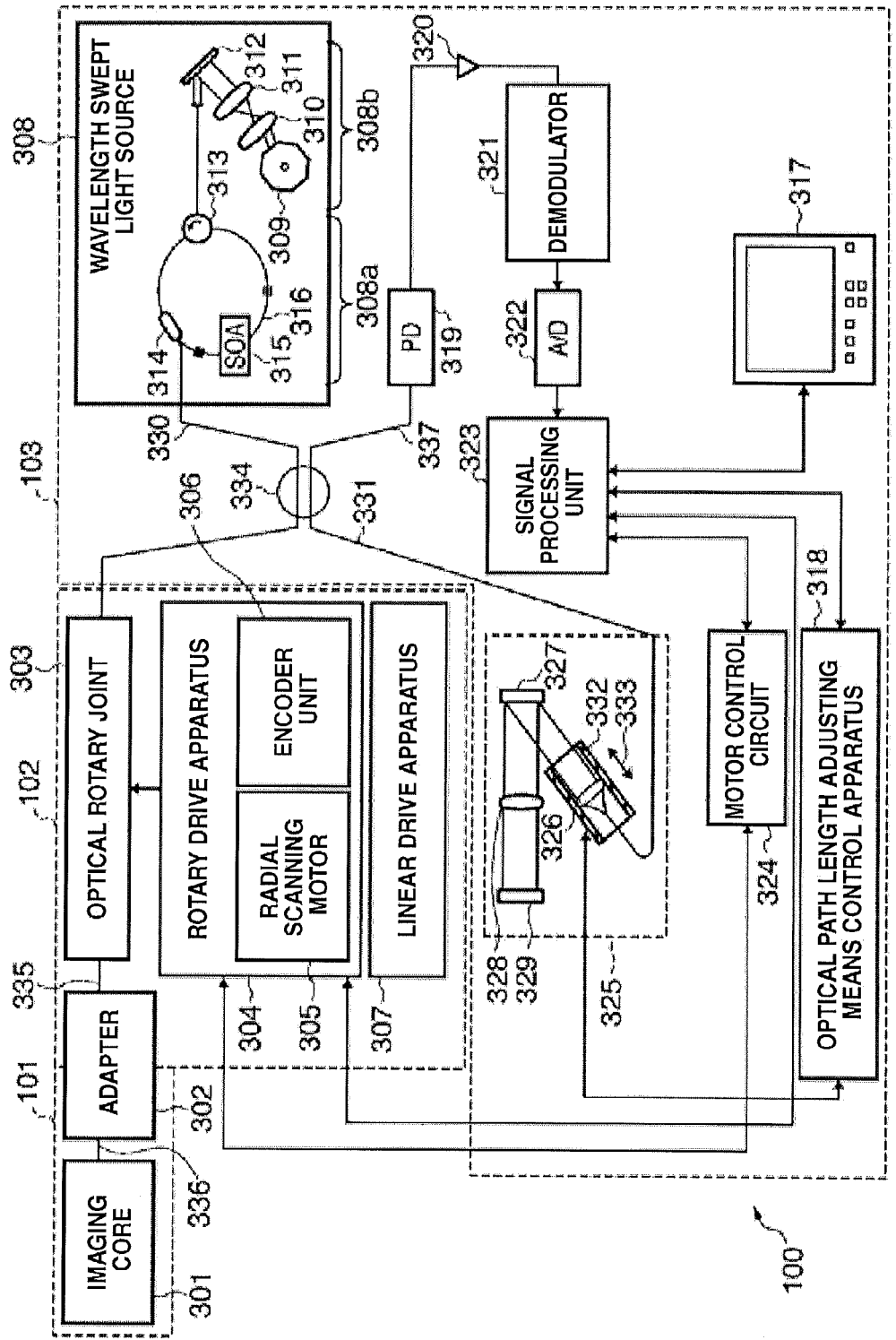
FIG. 3 is a diagram showing a functional constitution of the optical frequency domain imaging apparatus for diagnosis utilizing wavelength sweep 100.

FIG. 3 is a diagram showing a functional constitution of the optical frequency domain imaging apparatus utilizing wavelength sweep 100.

A reference numeral 308 indicates a wavelength swept light source and a swept laser is used thereto. The wavelength swept light source 308S using the wept Laser is one kind of an extended-cavity laser which is composed of an optical fiber 316 coupled with a SOA 315 (semiconductor optical amplifier) in a ring shape and a polygon scanning filter (308b).

The light outputted from the SOA 315 advances inside the optical fiber 316 and enters into the polygon scanning filter 308b and here, the wavelength selected light is amplified by the SOA 315 and finally, is outputted from a coupler 314.

In the polygon scanning filter 308b, the wavelength is selected by using the combination of a diffraction grating 312 for light-splitting the light and a polygon mirror 309. Specifically, the light light-split by the diffraction grating 312 is focused on the surface of the polygon mirror 309 by two pieces of lens (310, 311). Thus, it happens that only the light having wavelength, which is perpendicular to the polygon mirror 309 returns to the same optical path and is outputted from the polygon scanning filter 308b, so that by rotating the polygon mirror 309, it is possible to carry out time sweep of the wavelength.

With respect to the polygon mirror 309, for example, a 32-facets mirror is used and a rotation speed thereof is around 50000 rpm. Depending on a wavelength sweep system in which the polygon mirror 309 and the diffraction grating 312 are combined, it is possible to employ wavelength sweep of a high speed and a high power output.

The light of the wavelength swept light source 308 which is outputted from the coupler 314 enters into one end of a first single mode fiber 330 and transmitted to the distal end side. The first single mode fiber 330 is coupled optically with a second single mode fiber 337 and a third single mode fiber 331 in a photo coupler unit 334 on the way. Therefore, the light entered into the first single mode fiber 330 is transmitted by being split into maximum three optical paths depending on this photo coupler unit 334.

There is provided, on the distal end side from the photo coupler unit 334 of the first single mode fiber 330, with an optical rotary joint (photo coupling unit) 303 inside the rotary drive apparatus 204, which couples between a non-rotation unit (fixed unit) and a rotation unit (rotational drive unit) and which transmits the light.

Further, the distal end side of a fourth single mode fiber 335 inside the optical rotary joint (photo coupling unit) 303 is connected with a fifth single mode fiber 336 of the optical probe unit 101 freely detachably through an adaptor 302. Thus, the light from the wavelength swept light source 308 is transmitted to the fifth single mode fiber 336 which is inserted into the inside of the imaging core 301 and which is drivable rotationally.

The transmitted light is illuminated while being radially operated from the distal end side of the imaging core 301 with respect to the biological tissue of inside the body cavity. Then, a portion of the reflected light scattered at the surface or in the inside of the biological tissue is taken-in by the imaging core 301 and returns to the first single mode fiber 330 side by way of the opposite optical path. Further, a portion thereof is moved to the second single mode fiber 337 side by the photo coupler unit 334, is emanated from one end of the second single mode fiber 337, and is light-received by a photo detector (for example, photodiode 319).

Note that the rotational drive unit side of the optical rotary joint 303 is driven rotationally by a radial scanning motor 305 of a rotary drive apparatus 304. Also, the rotary angle of the radial scanning motor 305 is detected by an encoder unit 306. Further, the scanner & pull-back unit 102 includes a linear drive apparatus 307 and defines axial direction movement of the imaging core 301 based on an instruction from a signal processing unit 323.

On the other hand, a variable mechanism 325 of the optical path length for fine-adjusting the optical path length of the reference light is provided at the distal end on the opposite side of the photo coupler unit 334 of the third single mode fiber 331.

The variable mechanism 325 of this optical path length is provided with the optical path length changing means for changing the optical path length which corresponds to the fluctuation of the length thereof such that the fluctuation of the length of the individual optical probe unit 101 can be absorbed in case of using the optical probe unit 101 by being exchanged.

The third single mode fiber 331 and a collimating lens 326 are provided on a one-axis stage 332 which is freely movable in the optical axial direction thereof as shown by an arrow 333, and they form the optical path length changing means.

Specifically, the one-axis stage 332 functions as the optical path length changing means having such an amount of variable range of optical path length, which can absorb the fluctuation of the optical path length of the optical probe unit 101 in case of exchanging the optical probe unit 101. Further, the one-axis stage 332 is also provided with a function as an adjusting means for adjusting an offset. For example, even in a case in which the distal end of the optical probe unit 101 is not closely-attached to the surface of the biological tissue, it is possible, by changing the optical path length by the one-axis stage, to set it in a state of interfering with the reflected light from the surface position of the biological tissue.

The light whose optical path length is fine-adjusted by the variable mechanism 325 of the optical path length is mixed with the light obtained from the first single mode fiber 330 side by the photo coupler unit 334 which is provided on the way of the third single mode fiber 331 and it is received by the photo diode 319.

The interference light which is received by the photo diode 319 in this manner is photoelectrically converted and amplified by an amplifier 320 and thereafter, is inputted to a demodulator 321. In this demodulator 321, a demodulation process for extracting only the signal component of the interference light is carried out and the output thereof is inputted to an A/D converter 322 as the interference light signal.

In the A/D converter 322, there is produced digital data "interference light data" of one line by sampling the interference light signal, for example, for 2048 points by 180 MHz. Note that the reason why the sampling frequency is set to be 180 MHz is because it is on the assumption that about 90% of the cycle (12.5 μsec) of the wavelength sweep is to be extracted as the digital data of 2048 points in case of setting the repeat frequency of the wavelength sweep to be 40 kHz and it is not especially limited by this aspect.

The interference light data per line unit produced in the A/D converter 322 is inputted to the signal processing unit 323. In case of a measurement mode, in the signal processing unit 323, the interference light data are frequency-decomposed depending on an FFT (Fast Fourier Transform) and then, there are generated data in the depth direction, and by coordinate-converting those data, there is formed a tomographic image at each position inside the blood vessel and it is outputted to an LCD monitor 317 (which corresponds to reference numeral 113 in FIG. 1) by a predetermined frame rate.

The signal processing unit 323 is further connected with an optical path length adjusting means control apparatus 318. The signal processing unit 323 carries out the control of the position of the one-axis stage 332 through the optical path length adjusting means control apparatus 318. Also, the signal processing unit 323 is connected with a motor control circuit 324 and receives a video synchronization signal of the motor control circuit 324. In the signal processing unit 323, the generation of the tomographic image is carried out in synchronization with the received video synchronization signal.

In addition, the video synchronization signal of this motor control circuit 324 is transmitted also to the rotary drive apparatus 304 and the rotary drive apparatus 304 outputs the drive signal in synchronization with the video synchronization signal.

<4. Whole Constitution of Optical Probe Unit>

Next, it will be explained with respect to the whole constitution of the optical probe unit 101 by using FIG. 4. As shown in FIG. 4, the optical probe unit 101 is constituted by a long-sized catheter sheath 401 to be directly inserted into a body cavity such as a blood vessel and the like, and a connector unit 402 which is not inserted inside into the body cavity in order to be steered by a user and which is arranged on the hand-side of a user. At the distal end of the catheter sheath 401, a tube 403 for a guide wire lumen is formed, and the catheter sheath 401 is formed as a lumen which is continuous from a connection portion of the tube 403 for the guide wire lumen toward a connection portion with the connector unit 402 (here, see FIG. 5A and FIG. 5B for details).

In the inside of a lumen of a catheter sheath 401, there is inserted an imaging core 420, which includes a housing 421 provided with a transmitting and receiving unit for transmitting & receiving the measurement light and a drive shaft 422 transmitting drive force for rotating the housing, approximately over the full length of the catheter sheath 401.

The connector unit 402 is composed of a hand-side portion 402a constituted integrally at the proximal end of the catheter sheath 401 and a connection connector 402b constituted integrally at the proximal end of the drive shaft 422.

An anti-kink protector 411 is provided at a boundary portion between the hand-side portion 402a and the catheter sheath 401. Thus, a predetermined rigidity is maintained and it is possible to prevent a bend (kink) caused by a rapid change.

The proximal end of the connection connector 402b (see FIG. 7 for details) is constituted so as to be connectable with the scanner & pull-back unit 102 (see FIG. 8A and FIG. 8B for details) which will be described later.

<5. Constitution of Distal End Portion of Optical Probe Unit>

Figure 5B:
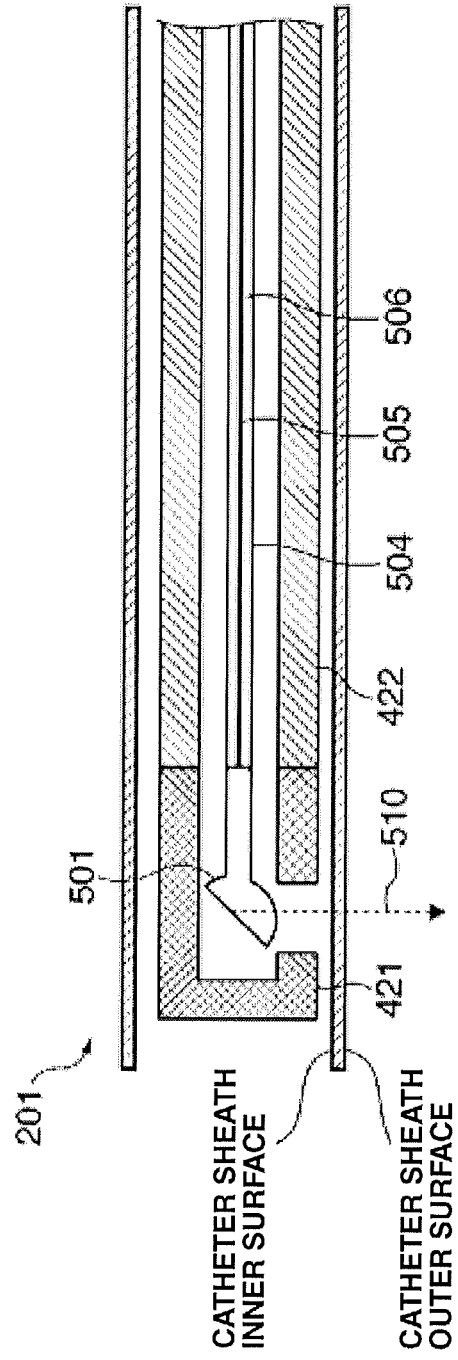
FIG. 5B is a diagram showing a constitution of a distal end portion of an optical probe unit.

Next, it will be explained with respect to a constitution of the distal end portion of the optical probe unit 101 by using FIG. 5A and FIG. 5B. As shown in FIG. 5A, in the inside of the lumen of the catheter sheath 401, there are passed-through the imaging core 420, provided with the housing 421 in which a transmitting and receiving unit 501 for transmitting the measurement light and for receiving the reflected light is arranged and the drive shaft 422 which transmits a drive force for rotating the housing, over approximately the full length thereof, and the optical probe unit 101 is formed.

In the transmitting and receiving unit 501, the measurement light is transmitted toward the tissue inside the body cavity and concurrently, reflected light from the tissue inside the body cavity is received.

The drive shaft 422 is formed in a coil shape, and there is arranged a signal wire (single mode optical fiber) in the inside thereof.

The housing 421 forms a shape including a cut portion at a portion of a short cylindrical shaped metal pipe and is shaped by a cutting out from a lump of metal, by MIM (metal powder injection molding) or the like. The housing 421 includes the transmitting and receiving unit 501 in the inside and the proximal end side thereof is connected with the drive shaft 422. Also, there is provided on the distal end side with a short coil shaped elastic member 502.

The elastic member 502 is a member obtained by forming a stainless steel wire material in a coil shape and owing to a fact that the flexible member 502 is arranged on the distal end side, lodging inside the catheter sheath is prevented when the imaging core 420 is moved forward and backward.

A reference numeral 503 indicates a reinforcement coil and is provided for the purpose of preventing rapid bending of the distal end portion of the catheter sheath 401.

A tube for guide wire lumen 403 includes a lumen for guide wire into which a guide wire is insertable. The tube for guide wire lumen 403 is used for accepting the guide wire inserted beforehand into the body cavity such as the blood vessel and for guiding the catheter sheath 401 until the target lesion depending on the guide wire.

It is possible for the drive shaft 422 to make the transmitting and receiving unit 501 perform rotational movement and axial direction movement with respect to the catheter sheath 401, and it is constituted, for example, by a multiple and multi-layered closely-attached coil or the like composed of a metal wire of a stainless steel or the like which is flexible and also has a characteristic in which rotation is well transmittable.

Also, FIG. 5B is a view showing a sectional constitution of the imaging core 420 schematically. As shown in FIG. 5B, the lateral illumination type ball lens (transmitting and receiving unit) 501 is arranged inside of the housing 421 and an optical fiber 504 constituted by a clad unit 506 and a core portion 505 is arranged inside of the drive shaft 422. Note that the measurement light transmitted from the transmitting and receiving unit 501 is illuminated onto the biological tissue of the body cavity by passing through the catheter sheath inner surface and the catheter sheath outer surface (see arrow 510).

<6. Constitution of Whole Imaging Core>

Figure 6:
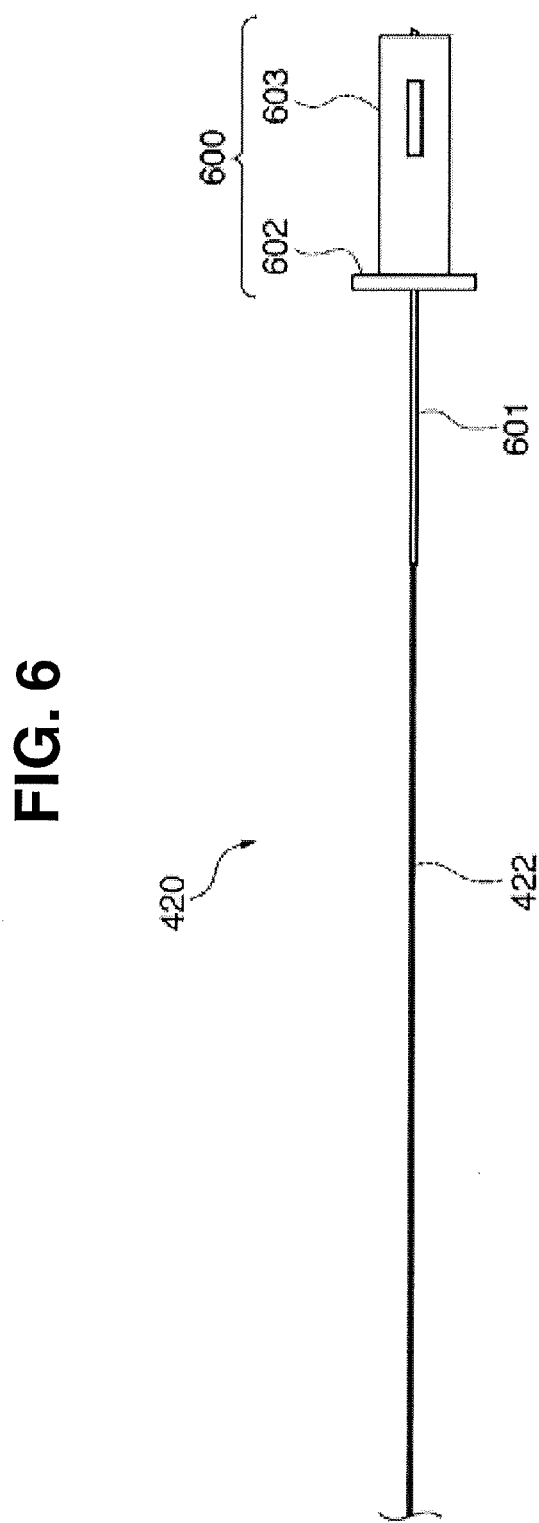
FIG. 6 is a diagram showing a whole constitution of an imaging core.

Next, it will be explained with respect to the whole constitution of the imaging core 420. FIG. 6 is a diagram showing the whole constitution of the imaging core 420. As shown in FIG. 6, on the proximal end side of the imaging core 420, there is attached a connector apparatus 600 which is optically connected with an optical adaptor inside the rotationally drive unit (details will be described later) when the connection connector 402b is connected to the scanner & pull-back unit 102 and concurrently, which transmits the rotationally drive force from the rotational drive unit to the drive shaft 422.

The connector apparatus 600 is provided with a connector fixing member 603 in which an APC optical connector (not shown) is arranged inside thereof and a flange 602 for fixing the connector fixing member 603 in the inside on the proximal end side of the connection connector 402b in a freely rotatable manner.

Note that it is assumed that the drive shaft 422 is joined with an APC optical connector which is arranged inside of the connector apparatus 600 through a connection pipe 601.

<7. Constitution of Connection Connector>

Figure 7:
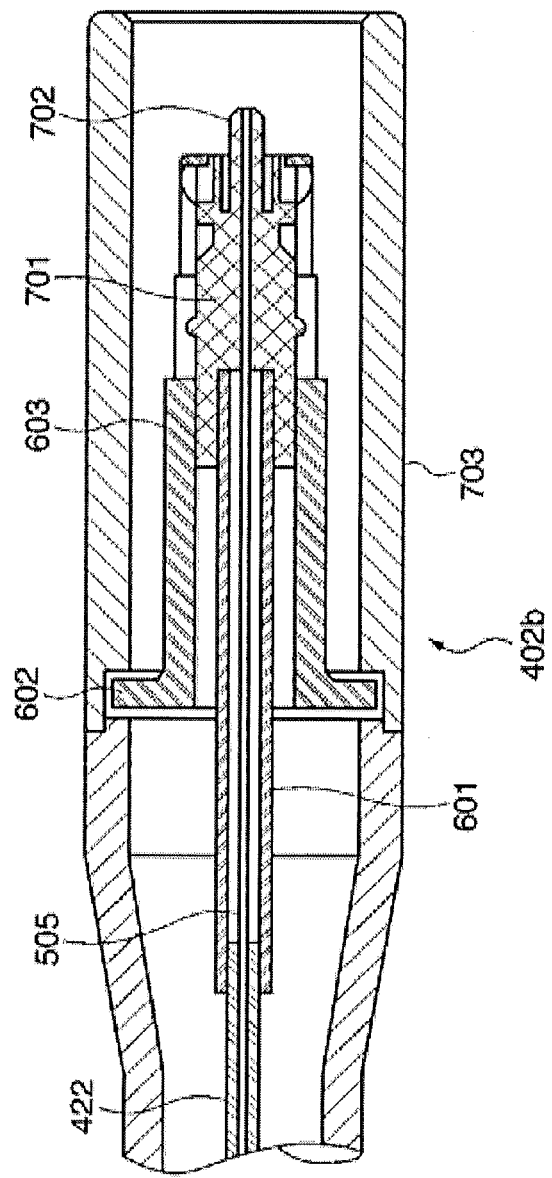
FIG. 7 is a diagram showing a constitution of a rear end portion of an optical probe unit.

Next, It will be explained with respect to a sectional constitution of the connection connector 402b by using FIG. 7. FIG. 7 is a sectional view showing an inside constitution on the proximal end side of the connection connector 402b.

As shown in FIG. 7, at the proximal end of the connection connector 402b, there is arranged a connector (APC optical connector) 701 for optical fiber and thus, the optical fiber 504 is optically connected with the optical adaptor which is arranged at a rotational drive unit inside of the scanner & pull-back unit 102.

The APC optical connector 701 is joined with the drive shaft 422 through the connection pipe 601. Also, the APC optical connector 701 is arranged inside of the connector fixing member 603 having a hollow tubular shape, and holds and fixed an end portion of the optical fiber 504 in which a ferrule 702 is provided at the distal end thereof. The end portion (connection surface) of the optical fiber 504 is processed in an APC type, in which a predetermined inclination angle is formed, with respect to the optical proceeding direction (rotation axial direction) in order to prevent from occurring the noise by the optical reflection at the end surface. The connector fixing member 603 includes the disc-shaped flange 602 at the distal end side end portion and is held in the inside of a housing 703 of the connection connector 402b in a freely rotatable manner.

the connector fixing member 603 carries out the positioning in the circumferential direction of the APC optical connector 701 in cooperation with the adapter fixing member on an occasion of coupling with the optical adaptor.

<8. Inside Constitution of Scanner & Pull-back Unit 102>

Figure 8A:
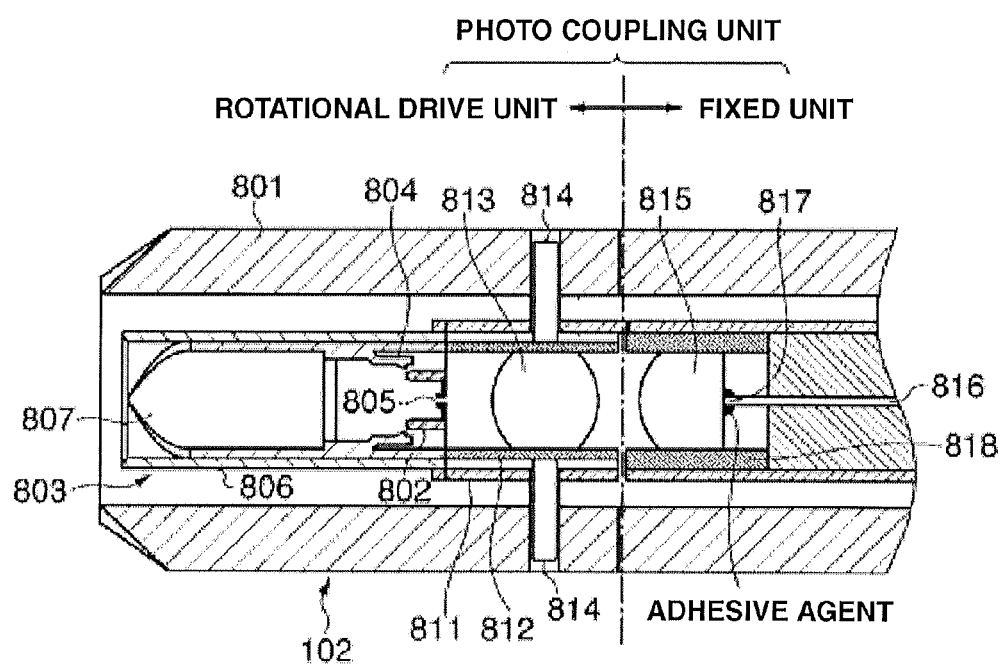
FIG. 8A is a diagram showing a constitution of a photo coupling unit in a scanner & pull-back unit.
Figure 8B:
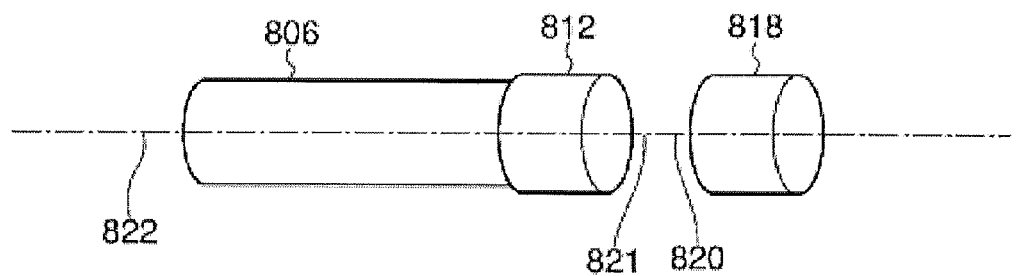
FIG. 8B is a diagram showing a constitution of a photo coupling unit in the scanner & pull-back unit.

Next, it will be explained with respect to an inside constitution of the scanner & pull-back unit 102. FIG. 8A and FIG. 8B are diagrams showing the inside constitution of the scanner & pull-back unit 102. In FIG. 8A and FIG. 8B, the page face left side indicates a rotational drive unit and the page face right side indicates a fixed unit.

In FIG. 8A, a reference numeral 801 indicates a housing of the scanner & pull-back unit 102 and the housing 703 of the connection connector 402b is fitted on the inner surface thereof. A reference numeral 802 indicates the optical adaptor, which is coupled with the APC optical connector 701. A reference numeral 803 indicates an adapter fixing member, which is formed in a hollow tubular shape and the optical adaptor 802 is fixed in the inside thereof so as to be unrotatable relatively. The adapter fixing member 803 carries out the positioning in the circumferential direction of the APC optical connector 701 in cooperation with the connector fixing member 603 on an occasion of coupling with the APC optical connector 701.

The adapter fixing member 803 is constituted by a protection tube 806 for defining the outer surface and a main body 807 which is fixed on the inner surface of the protection tube 806 and which defines the inner surface of the adapter fixing member 803.

A pair of claws 804 are formed on the inner surface of the adapter fixing member 803. The pair of claws 804 are engaged with the APC optical connector 701 and integrate the APC optical connector 701 and the optical adaptor 802 tightly.

Note that at the optical adaptor 802, there is formed a hole 805 having female type structure, which accepts the ferrule 702 of the APC optical connector 701.

A reference numeral 811 indicates a lens fixing sleeve supporting portion and an optical lens 813 is fixed in the inside thereof by a lens fixing sleeve 812. Note that it is assumed that the lens fixing sleeve 812 is fixed position-adjustably by set screws 814 with respect to the lens fixing sleeve supporting portion 811.

On the other hand, at the fixed unit of the scanner & pull-back unit 102, there is arranged a lens fixed unit 818 and on the lens fixed unit 818, there is fixed a collimator lens 815. Also, the collimator lens 815 is connected with an optical fiber 816. Thus, it becomes a situation in which the reflected light radiated from the ferrule 702 of the APC optical connector 701 enters into the connected optical fiber 816 through the optical lens 813 and the collimator lens 815. On the other hand, it becomes a situation in which the measurement light optically guided from the optical fiber 816 is emanated from the collimator lens 815 and enters into the ferrule 702 of the APC optical connector 701 in a non-contact manner through the optical lens 813.

In other words, in the scanner & pull-back unit 102, there is formed a photo coupling unit for carrying out the optical transmission between the rotational drive unit and the fixed unit in a non-contact manner.

FIG. 8B is a diagram indicating the photo coupling unit schematically. As shown in FIG. 8B, the optical axis 821 which is determined by the position of the lens fixing sleeve 812 on the rotational drive unit side usually coincides with the rotation axis 822 of the rotational drive unit and also, coincides with the optical axis 820 which is determined by the position of the lens fixed unit 818 on the fixed unit side.

<9. Detailed Constitution of Signal Processing Units 214, 323>

Figure 9:
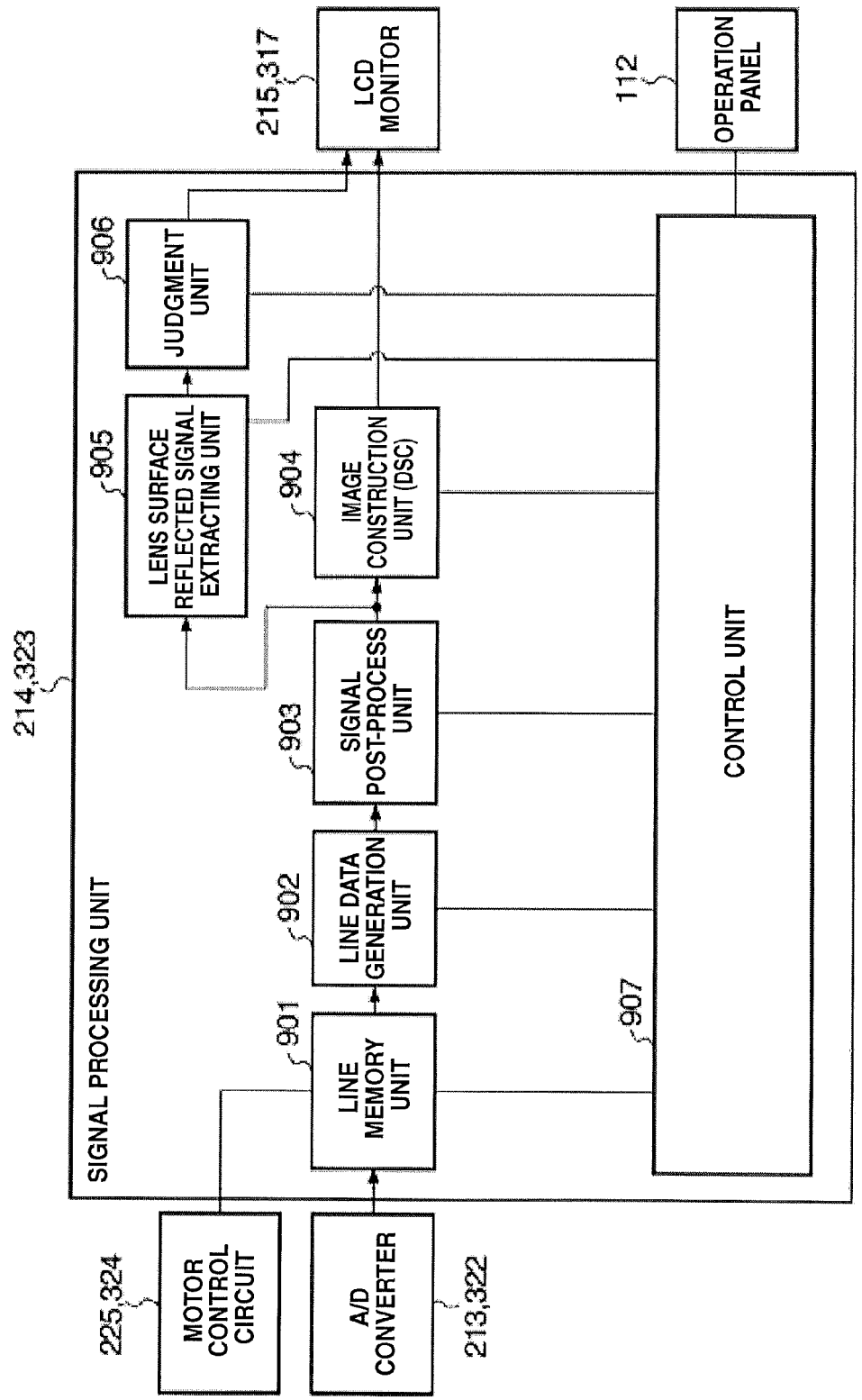
FIG. 9 is a diagram showing a detailed constitution of a signal processing unit and a related function block.

Next, by using FIG. 9, it will be explained with respect to an outline of a process in the signal processing units 214, 323 of the imaging apparatus for diagnosis 100. FIG. 9 is a diagram showing a detailed constitution of the signal processing units 214, 323 and an associated functional block.

The interference light data produced by the A/D converter 213, 322 is processed in the line memory unit 901 such that the number of lines per one rotation of the radial scanning motor becomes 512 lines by using the signal of the encoder unit 206 or 306 of the radial scanning motor 205 or 305, which is outputted from the motor control circuit 225, 324 and thereafter, it is outputted to the line data generation unit 902 in the succeeding stage.

In the line data generation unit 902, line data are generated by applying a line addition-averaging process, a filtering process, a logarithmic conversion process or the like with respect to the interference light data and by generating the interference light intensity data in the depth direction of the biological tissue and thereafter, the generated line data are outputted to the signal post-processing unit 903 in the succeeding stage. In the signal post-processing unit 903, a contrast adjustment, a brightness adjustment, a gamma correction, a frame correlation, a sharpness process and the like are carried out with respect to the line data and it is outputted to the image construction unit (DSC) 904.

In the image construction unit 904, a tomographic image is generated owing to a fact that the line data series of the polar coordinate are Rθ-converted and thereafter, it is converted to a video signal and the tomographic image is displayed on the LCD monitor 215 or 317. It should be noted, in this exemplified embodiment, that it is assumed to generate the tomographic image from 512 lines as one example, but it is not to be limited by this number of lines.

Further, in the signal processing units 214, 323 of the imaging apparatus for diagnosis 100 relating to this exemplified embodiment, there are further provided with a lens surface reflected signal extracting unit 905 and a judgment unit 906 as a function (coupling state inspection function) for testing a coupling state in the photo coupling unit. Hereinafter, while referring to FIG. 10 and FIG. 11, it will be explained in detail with respect to the coupling state inspection function which is realized by the lens surface reflected signal extracting unit 905 and the judgment unit 906.

<10. Explanation of Coupling State Inspection Function (Lens Surface Reflected Signal Extracting Unit)>

Figure 10:
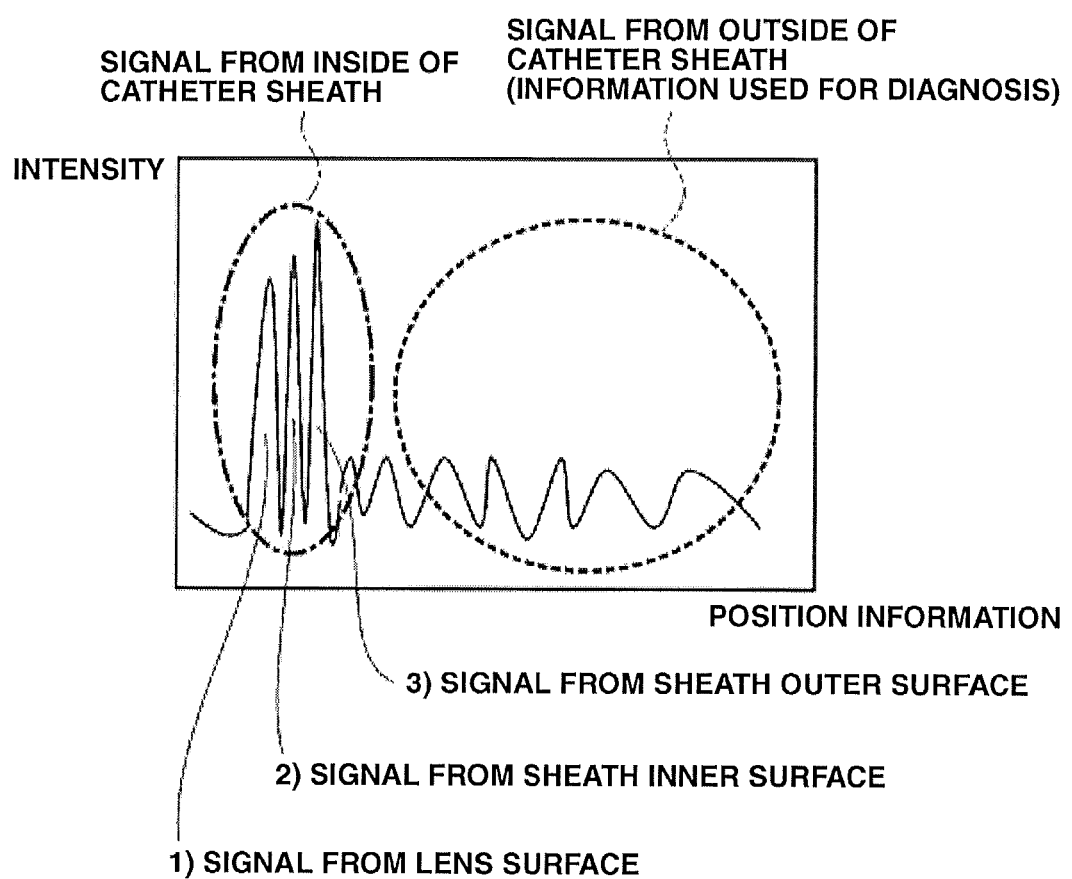
FIG. 10 is a diagram showing one example of line data used for generation of a tomographic image.

FIG. 10 is a diagram showing the line data processed in the signal processing units 214, 323. In FIG. 10, the horizontal axis denotes positional information and the vertical axis denotes intensity (that is, FIG. 10 shows intensity distribution of interference light from transmission and reception position to position in predetermined depth direction inside body cavity).

It is possible for the line data generated based on the interference light obtained from the transmitting and receiving unit 501 shown in FIG. 5B to be roughly classified into signals from the inside of the catheter sheath 401 and signals which are signals from the outside of the catheter sheath 401 and which includes information used for the diagnosis, as shown in FIG. 10.

Within those, in the signal from the inside of the catheter sheath 401, there are further included 1) signals from the lens (transmitting and receiving unit 501) surface, 2) signals from the inner surface of the catheter sheath 401 and 3) signals from the outer surface of the catheter sheath 401.

Within those, the signal from the lens surface becomes a constant intensity regardless of a state of the optical probe unit 101 (occurrence of stuck state, invasion of blood into catheter sheath 401, vibration of transmitting and receiving unit or the like). In other words, it is possible for the signal from the lens surface to be referred to as the signal indicating the coupling state of the photo coupling unit of the scanner & pull-back unit 102.

Consequently, in the lens surface reflected signal extracting unit 905, the signal intensity from the lens surface is extracted within the line data outputted from the signal post-processing unit 903. Note that the extraction of the signal intensity from the lens surface in the lens surface reflected signal extracting unit 905 is carried out at least for the line data for one rotation of the transmitting and receiving unit (that is, for 512 lines). Thus, it is possible to discriminate the change of the signal intensity from the lens surface in one rotation of the transmitting and receiving unit.

<11. Explanation of Coupling State Inspection Function (Judgment Unit)>

Figure 11:
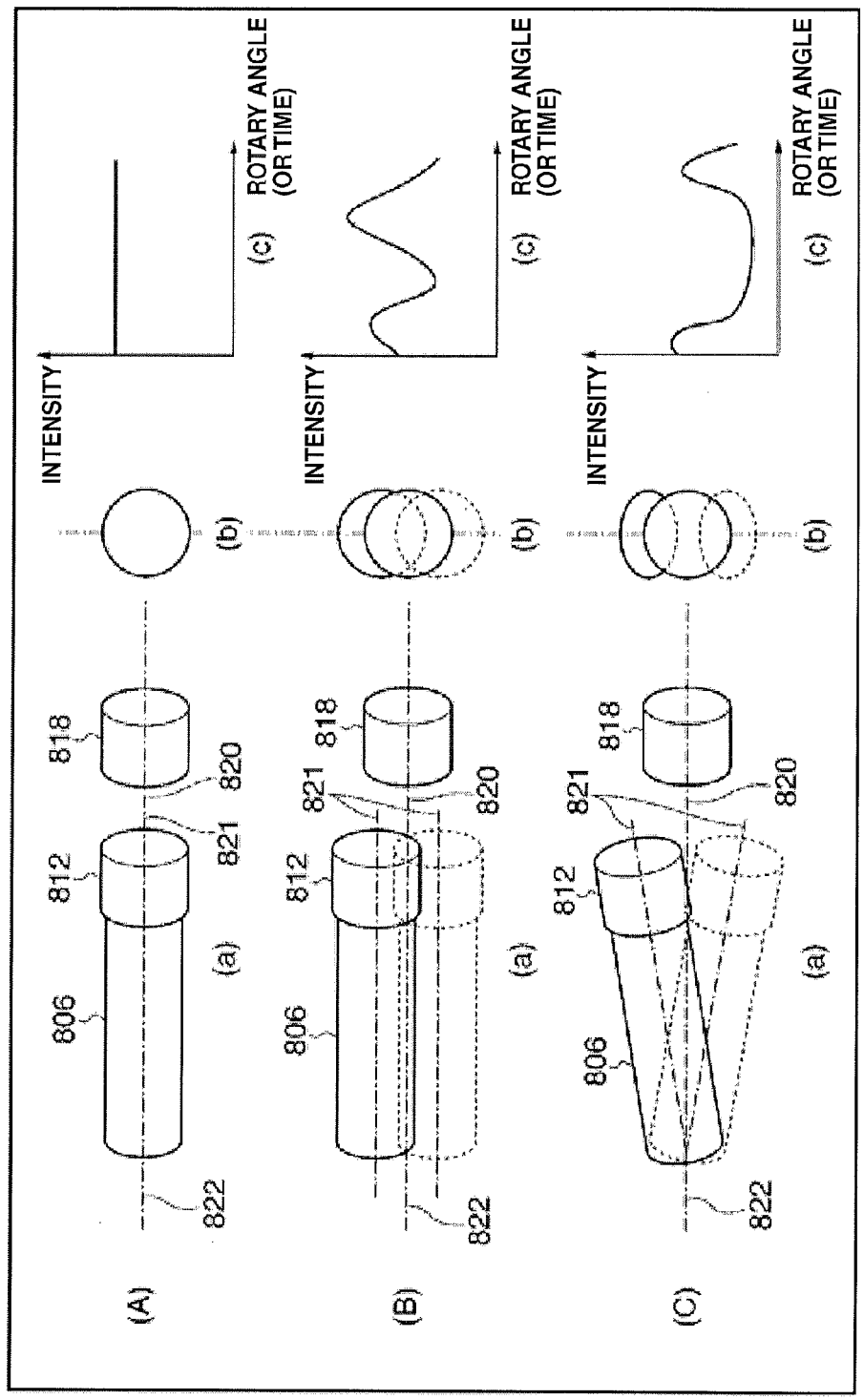
FIG. 11 is a diagram showing a relation between a coupling state of a photo coupling unit and a time change in intensity reflected from a lens surface.

FIG. 11 are diagrams showing the relation between coupling states in the photo coupling unit and the intensity of the signal from the lens surface in one rotation of the transmitting and receiving unit.

Symbols (A) in FIG. 11 show a case in which the optical axis 821 determined by the position of the lens fixing sleeve 812 on the rotational drive unit side and the rotation axis 822 of the rotational drive unit coincide with each other and also, they coincide with the optical axis 820 determined by the position of the lens fixed unit 818 on the fixed unit side.

As shown in (a) of (A) in FIG. 11, in a case in which the optical axis 820, the optical axis 821 and the rotation axis 822 coincide with each other, the cross-section position of the lens fixing sleeve 812 and the cross-section position of the lens fixed unit 818 always coincide with each other regardless of the rotary angle on the rotational drive unit side (see (c) of (A) in FIG. 11).

In this case, the signal intensity from the lens surface becomes a constant regardless of the rotary angle on the rotational drive unit side (see (c) of (A) in FIG. 11).

On the other hand, symbols (B) in FIG. 11 show a case in which the optical axis 821 determined by the position of the lens fixing sleeve 812 on the rotational drive unit side is deviated with respect to the rotation axis 822 of the rotational drive unit and thus, it is deviated with respect to the optical axis 820 determined by the position of the lens fixed unit 818 on the fixed unit side.

As shown in (a) of (B) in FIG. 11, in a case in which the optical axis 821 and the rotation axis 822 are deviated each other in parallel and thus, the optical axis 820 and the optical axis 821 are deviated each other in parallel, it becomes a situation in which the cross-section position of the lens fixing sleeve 812 and the cross-section position of the lens fixed unit 818 are always deviated each other in parallel by the rotary angle on the rotational drive unit side (see (b) of (B) in FIG. 11).

In this case, it becomes a situation in which the signal intensity from the lens surface varies periodically according to the rotary angle on the rotational drive unit side (see (c) of (B) in FIG. 11).

Also, symbols (C) in FIG. 11 show a case in which the optical axis 821 determined by the position of the lens fixing sleeve 812 on the rotational drive unit side is deviated with a predetermined angles with respect to the rotation axis 822 of the rotational drive unit and thus, it is deviated with a prede-termined angles with respect to the optical axis 820 determined by the position of the lens fixed unit 818 on the fixed unit side.

As shown in (a) of (C) in FIG. 11, the optical axis 821 and the rotation axis 822 are deviated each other with a predetermined angles and thus, in a case in which the optical axis 821 is deviated with a predetermined angles with respect to the optical axis 820, it becomes a situation in which the cross-section of the lens fixing sleeve 812 always faces at a predetermined angles with respect to the cross-section of the lens fixed unit 818 by the rotary angle on the rotational drive unit side (see (b) of (C) in FIG. 11).

In this case, the signal intensity from the lens surface lowers as the whole and concurrently, it becomes a situation in which it varies periodically according to the rotary angle on the rotational drive unit side (see (c) of (C) in FIG. 11).

In light of such a characteristic, in the judgment unit 906, a threshold having a predetermined range is provided with respect to the variation widths (difference between maximum value and minimum value) of the signal intensity from the lens surface, which is extracted in the lens surface reflected signal extracting unit 905, and in a case in which the variation widths exceed the predetermined threshold, it is judged that the coupling state is abnormal and an alarm is outputted to the LCD monitors 215, 317.

<12. Flow of Coupling State Inspection Process>

Figure 12:
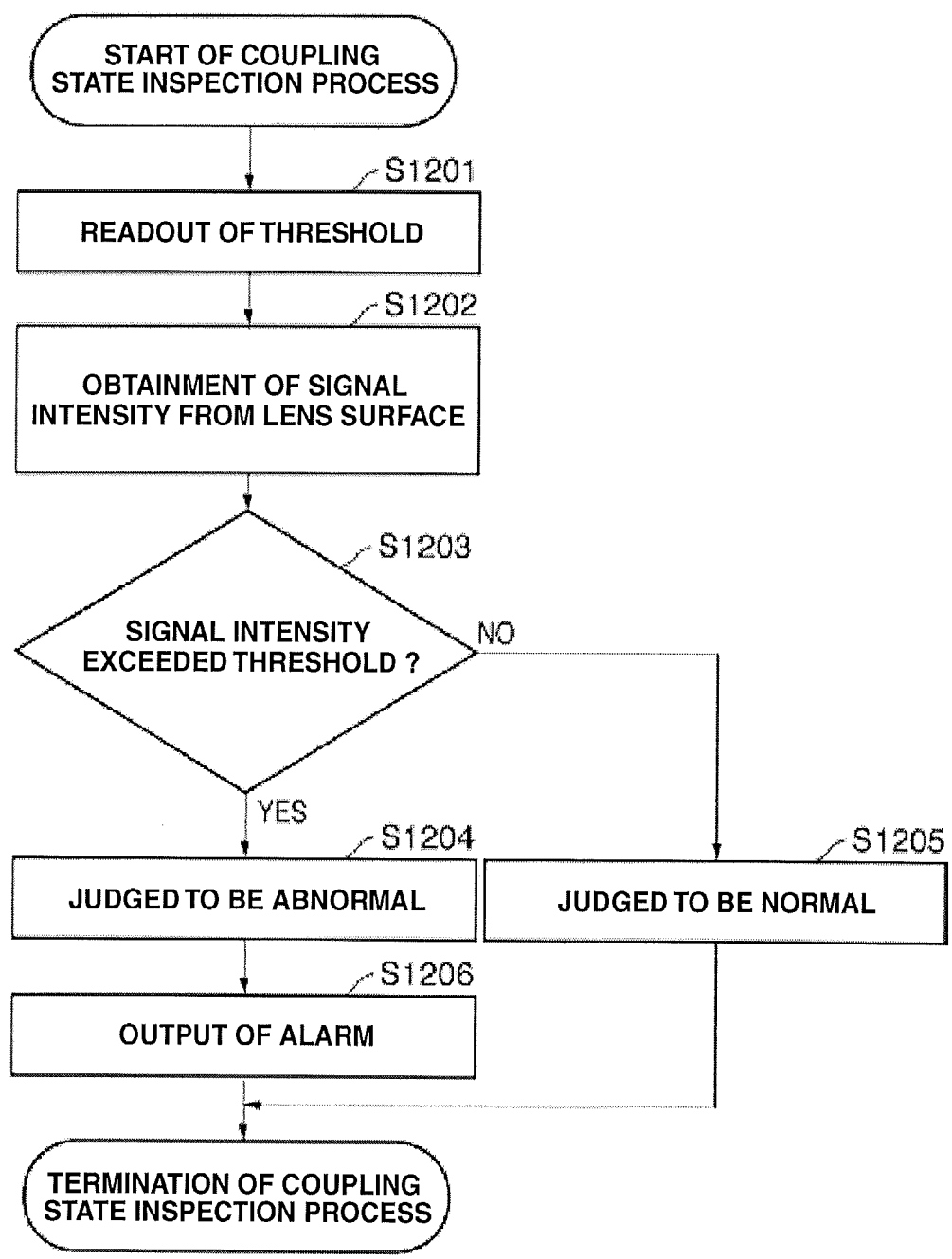
FIG. 12 is a flowchart showing a flow of a coupling state inspection process.

Next, it will be explained with respect to a flow of a coupling state inspection process by using FIG. 12. FIG. 12 is a flowchart showing a flow of a coupling state inspection process in the imaging apparatus for diagnosis 100 relating to this exemplified embodiment.

In the operation panel 112, when a coupling state inspection process start instruction of the photo coupling unit is inputted, the coupling state inspection process shown in FIG. 12 is started.

In step S1201, the judgment unit 906 reads out the threshold which is registered in the control unit 907 beforehand.

In step S1202, the lens surface reflected signal extracting unit 905 extracts signal intensity from the lens surface based on the line data outputted from the signal post-processing unit 903. Note that it is assumed that the signal intensity extracting from the lens surface at that time is at least for one rotation of the transmitting and receiving unit for (for line data of 512 lines).

In step S1203, the judgment unit 906 judges whether or not the variation width of the signal intensity which was extracted in step S1202 exceeds the range of the threshold which was read out in step S1201.

In step S1203, in a case in which it was judged that the variation width of the signal intensity does not exceed the range of the threshold, the process proceeds to step S1205 and it is judged that the of coupling state of the photo coupling unit is normal, and the coupling state inspection process is terminated.

On the other hand, in step S1203, in a case in which it was judged that the variation width of the signal intensities exceeds the range of the threshold, the process proceeds to step S1204 and it is judged that the of coupling state of the photo coupling unit is abnormal, and the process proceeds to step S1 206.

In step S1 206, the judgment unit 906 outputs an alarm to the LCD monitors 215, 317 and notifies it to the user and thereafter, terminates the coupling state inspection process.

In this manner, on an occasion when imaging the tomographic image, it becomes possible to confirm the coupling state of the photo coupling unit by executing the coupling state inspection process beforehand. Note that as the result of the coupling state inspection process, in a case in which the alarm is outputted, the user matches the optical axis 821 of the lens fixing sleeve 812 with the rotation axis 822 of the rotational drive unit by adjusting the position of the lens fixing sleeve 812 by the set screw 814. Thus, it becomes possible to match with the optical axis 820 by the position of the lens fixed unit 818 on the fixed unit side.

As clear from the explanation mentioned above, in the imaging apparatus for diagnosis relating to this exemplified embodiment, it was made to be a constitution in which the signal intensities from the lens surface within the generated line data are extracted at least over for one rotation of the transmitting and receiving unit, and the variation width of the intensities with respect to the rotary angles of the transmitting and receiving unit is judged.

According to this result, it becomes possible to confirm the deviation of the optical axis of the photo coupling unit in the scanner & pull-back unit.

Second Exemplified Embodiment

In the first exemplified embodiment mentioned above, on an occasion when the abnormality of the coupling state of the photo coupling unit is detected, it was assumed to be a constitution in which the variation width (difference between maximum value and minimum value) of the signal intensities from the lens surface is calculated, but the present invention is not limited by this.

For example, it is allowed to be a constitution in which an average value of the reflected signal intensities for one rotation of the transmitting and receiving unit is found out and the difference between the average value and a maximum value or a minimum value is calculated. Alternatively, it is allowed to be a constitution in which fluctuations of the signal intensities for one rotation of the transmitting and receiving unit are calculated.

Note that the intensity of the extracting signal is not limited by for one rotation of the transmitting and receiving unit, and it is also allowed to be for a plurality of rotations or to be for a predetermined time period.

Also, in the first exemplified embodiment mentioned above, it was assumed to be a constitution in which the judgment result in the judgment unit 906 is outputted to the LCD monitors 215, 317, but the present invention is not limited by this aspect. For example, it is allowed to be constituted such that a graph ((c) within (A) to (C) of FIG. 11) showing a change of the intensity of each signal for each rotation position of the transmitting and receiving unit 501, which is extracted in the lens surface reflected signal extracting unit 905, is generated, and the graph is outputted to the LCD monitors 215, 317.

Further, in the first exemplified embodiment mentioned above, it is on an assumption that the optical axis 820 determined by the position of the lens fixed unit 818 on the fixed unit side and the rotation axis 822 of the rotational drive unit coincide and it was made to be a constitution in which the position of the lens fixing sleeve 812 is adjusted by using the set screw 814 in a case in which the optical axis 821 and the optical axis 820 are deviated caused by a fact that the optical axis 821 determined by the position of the lens fixing sleeve 812 is deviated with respect to the rotation axis 822, but the present invention is not limited by this aspect.

A case in which the optical axis 820 determined by the position of the lens fixed unit 818 is deviated with respect to the rotation axis 822 is supposed, and it is also allowed for the lens fixed unit 818 to be constituted so as to fix position-adjustably. In this case, it becomes possible for the user to match the optical axis 821 with the optical axis 820 by adjusting the position of the lens fixed unit 818 with respect to the output of an alarm to the effect that the coupling state is abnormal.

The present invention is not to be limited by the exemplified embodiments described above and it is possible to employ various changes and modifications without departing from the spirit and the scope of the present invention. Therefore, the following claims are attached in order to open the scope of the present invention.

The present invention contains subject matter related to Japanese Patent Application JP2009-227840 filed in the Japanese Patent Office on Sep. 30, 2009, the entire contents of which being incorporated herein by reference.

The invention claimed is:

1. An imaging apparatus for diagnosis comprising:
   a probe including a transmitting and receiving unit adapted to transmit light transmitted from a light source continuously to an inside of a body cavity and concurrently, adapted to receive reflected light continuously from the inside of the body cavity, and the transmitting and receiving unit including a lens and a lens surface;
   a signal processing unit configured to generate a tomographic image of inside the body cavity based on the received reflected light from the transmitting and receiving unit while rotating the transmitting and receiving unit,
   a photo coupling unit configured to carry out an optical transmission between a rotational optical path of the imaging apparatus and a fixed optical path of the imaging apparatus;
   a lens surface reflected signal extracting unit configured to extract a signal intensity of a signal reflected from the lens surface within the reflected lights received by the transmitting and receiving unit at respective rotary angles of the transmitting and receiving unit during rotation; and
   a judgment unit configured to judge whether or not an optical axis of the fixed optical path at the photo coupling unit is deviated with respect to a rotation axis of the rotational optical path at the photo coupling unit by confirming whether or not the signal intensity of each signal reflected from the lens surface extracted by the lens surface reflected signal extracting unit at each rotary angle of the transmitting and receiving unit lies in a predetermined range.

2. The imaging apparatus for diagnosis according to claim 1, further comprising output means outputting alarm for informing that there exists abnormality on a coupling at the photo coupling unit in a case in which the intensity is judged, by the judgment unit, not to lie in the predetermined range.

3. The imaging apparatus for diagnosis according to claim 1, further comprising generation means generating a graph showing intensity change of each reflected light which is extracted by the lens surface reflected signal extracting unit with respect to each rotary angle of the transmitting and receiving unit.

4. The imaging apparatus for diagnosis according to claim 1, wherein the transmitting and receiving unit includes a reflection portion adapted for transmitting the light transmitted from the light source inside a body cavity.

5. The imaging apparatus for diagnosis according to claim 1, wherein the judgment unit judges whether or not the intensity of each reflected light which is extracted by the lens surface reflected signal extracting unit lies in the predetermined range with respect to at least for one rotation of the transmitting and receiving unit.

6. A method for controlling an imaging apparatus for diagnosis which includes a probe, the probe possessing a transmitting and receiving unit adapted to transmit light transmitted from a light source continuously to the inside of a body cavity and concurrently, adapted to receive reflected light continuously from the inside of the body cavity, the transmitting and receiving unit possessing a lens and a lens surface, a signal processing unit configured to generate a tomographic image inside the body cavity based on the obtained reflected light by obtaining the reflected light from the transmitting and receiving unit while rotating the transmitting and receiving unit, and including a photo coupling unit configured to carry out an optical transmission between a rotational optical path of the imaging apparatus and a fixed optical path of the imaging apparatus, the method comprising:

extracting signal intensities of signals reflected from the lens surface within the reflected lights received by the transmitting and receiving unit at respective rotary angles of the transmitting and receiving unit during rotation; and judging whether or not an optical axis of the fixed optical path at the photo coupling unit is deviated with respect to a rotation axis of the rotational optical path at the photo coupling unit by confirming whether or not the signal intensity of each signal reflected from the lens surface extracted in the extraction process at each rotary angle of the transmitting and receiving unit lies in a predetermined range.

7. The method of according to claim 6, further comprising an output process outputting alarm for informing that there exists abnormality on a coupling at the photo coupling unit in a case in which the intensity is judged, in the judgment process, not to lie in the predetermined range.

8. The method according to claim 6, further comprising a generation process generating a graph showing intensity change of each reflected light which is extracted in the extraction process with respect to each rotary angle of the transmitting and receiving unit.

9. The method according to claim 6, wherein the transmitting and receiving unit includes a reflection portion for transmitting the light transmitted from the light source inside a body cavity.

10. The method according to claim 6, wherein the judgment process judges whether or not the intensity of each reflected light which is extracted in the extraction process lies in the predetermined range with respect to at least for one rotation of the transmitting and receiving unit.

* * * * *